United States Patent
Lee et al.

(10) Patent No.: US 10,500,188 B1
(45) Date of Patent: Dec. 10, 2019

(54) USE OF A POLYENYLPYRROLE DERIVATIVE IN PREPARATION OF ANTI-ORAL CANCER DRUGS

(71) Applicant: TZU CHI UNIVERSITY, Hualien (TW)

(72) Inventors: Jeng-Woei Lee, Hualien (TW); Chia-Chen Lau, Jhubei (TW); Kuo-Feng Hua, Yilan (TW); Yulin Lam, Singapore (SG)

(73) Assignee: Tzu Chi University, Hualien (TW)

( * ) Notice: Subject to any disclaimer, the term of this patent is extended or adjusted under 35 U.S.C. 154(b) by 0 days.

(21) Appl. No.: 16/385,198

(22) Filed: Apr. 16, 2019

(30) Foreign Application Priority Data

Jan. 28, 2019 (TW) .............................. 108103177 A

(51) Int. Cl.
*A61K 31/40* (2006.01)
*A61K 31/4025* (2006.01)
*A61P 35/00* (2006.01)

(52) U.S. Cl.
CPC .......... *A61K 31/4025* (2013.01); *A61P 35/00* (2018.01)

(58) Field of Classification Search
CPC ....................................................... A61K 31/40
USPC ......................................................... 514/427
See application file for complete search history.

(56) References Cited

U.S. PATENT DOCUMENTS

2015/0284355 A1* 10/2015 Hua ..................... C07D 309/38
514/422

* cited by examiner

*Primary Examiner* — Raymond J Henley, III
(74) *Attorney, Agent, or Firm* — Rosenberg, Klein & Lee

(57) ABSTRACT

The present invention discloses use of a polyenylpyrrole derivative in preparation of an anti-oral cancer drugs. The polyenylpyrrole derivative synthesized by polyvinylpyrrole, auxarconjugatin A and 12E-isorumbrin inhibits the cell proliferation, migration, tumor sphere formation abilities and xenograft tumorigenicity of oral cancer cells.

9 Claims, 17 Drawing Sheets

USE OF A POLYENYLPYRROLE DERIVATIVE IN PREPARATION OF ANTI-ORAL CANCER DRUGS

BACKGROUND OF THE INVENTION

Field of the Invention

The present invention relates to a polyenylpyrrole derivative, especially to a polyenylpyrrole derivative used in preparation of anti-oral cancer drugs.

Description of Related Art

Statistics of the Ministry of Health and Welfare by 2016 showed that oral cancer is the 5th leading cause of cancer-related deaths in Taiwan. The age-of-onset of oral cancer is 40-70 in men. The oral cancer has become the 4th most fatal cancer in men since 2003.

The oral cancer is used to occur in the middle-aged. Yet the age of onset is getting earlier in recent years. Now the number of the patients with oral cancer aged 20-30 years old is gradually increasing and the mean age at death is 53 years, 10 years earlier than other cancers. The phenomenon is closely related to living environment and habits of modern people. According to statistics, over 70% patients with oral cancer have a habit of smoking or chewing betel nuts.

The oral cavity includes the lips, the buccal mucosa (the inside lining of the lips and cheeks), the teeth, the floor of the mouth below the tongue, the front two-thirds of the tongue, the bony roof of the mouth (hard palate), the gums and the small area behind the molar teeth. The oral cancer is the abnormal growths of cells occurred in the above areas of the oral cavity. Then the cancer cells invade surrounding normal tissues, spread to other parts of the body, impair normal functioning and further threaten the life.

Based on histology, the oral cancer includes squamous-cell carcinoma, minor salivary gland cancer, verrucous carcinoma, sarcoma, malignant melanoma, etc. but over 90% are oral squamous cell carcinoma (OSCC) and the most common sites are the buccal mucosa, the gums, the palate, the floor of the mouth and the lips.

Cytometaplasia caused by imbalanced gene regulation or mutations occurs when oral mucosa is continuously stimulated by risk factors. The risk factors for oral cancer includes smoking, alcohol consumption, chewing betel nuts, UV radiation, tooth decay, improper dentures, poor oral hygiene, long term malnutrition, virus infection (Human Papillomavirus, HPV16), etc.

In clinical practice, metaplasia or improper cell proliferation happens on mucosa surface to form leukoplakia, erythroplakia, erytholeukoplakia, ulcers, verrucous hyperplasia or oral mucosal fibrosis. The above all are oral potentially malignant disorders. After long term inflammation and irritation, these malignant disorders will eventually develop into oral cancer.

The common symptoms of oral cavity include ulcer in the mouth, lumps, erythroplakia, leukoplakia, together with enlarged cervical lymph node, inability to open the mouth, swallowing difficulties, etc. Most of the patients are painless in early stages. When the tumor grows and local necrosis occurs, patients may have abnormal pain caused by bacteria infection. Oral cancer cells often spread to lymph nodes around the neck-submandibular region, submental region, upper neck region, middle neck region and posterior neck region. The common sites for distant metastasis include lung, liver, bone, etc.

The treatment options for oral cancer available now includes surgical excision or removal of neck lymph nodes, chemotherapy and radiation therapy. Generally, surgery is the main modality of cancer management, used in conjunction with chemotherapy and radiation. The survival rate for stage 1 oral cancer is approximately 90% and the survival rate for stage 2 is about 80-90%. Yet the survival rate for patients at advanced stage 3 and stage 4 is only 30-50%. Thus there are still unmet medical needs that remain in prevention, diagnosis and treatment of oral cancer.

And there is a need to find out one of natural products with anti-tumor activity for preparing anti-oral cancer drugs.

SUMMARY OF THE INVENTION

Therefore it is a primary object of the present invention to provide a polyenylpyrrole derivative used in preparation of anti-oral cancer drugs owing to inhibition effect of polyenylpyrrole derivative on cell proliferation, migration, movement, tumor sphere formation abilities and xenograft tumorigenicity of oral cancer cells.

In order to achieve the above object, a polyenylpyrrole derivative used in preparation of anti-oral cancer drugs according to the present invention is used to inhibit oral cancer cells.

Preferably, the polyenylpyrrole derivative used in preparation of anti-oral cancer drugs has the following structural formula:

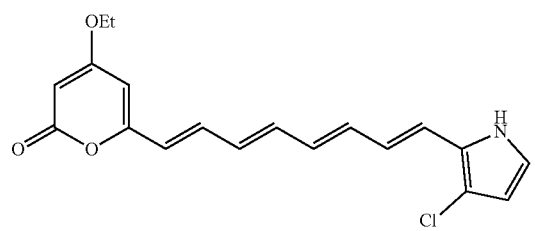 [SMILES: CCOc1cc(/C=C/C=C/C=C/C=C/c2[nH]ccc2Cl)oc(=O)c1]

Preferably, the oral cancer cell being habited by the polyenylpyrrole derivative is an oral squamous cell carcinoma (OSCC) cell.

Preferably, the polyenylpyrrole derivative used in preparation of anti-oral cancer drugs inhibits proliferation ability of the OSCC cell.

Preferably, the polyenylpyrrole derivative used in preparation of anti-oral cancer drugs inhibits migration ability of the OSCC cell.

Preferably, the polyenylpyrrole derivative used in preparation of anti-oral cancer drugs inhibits movement ability of the OSCC cell.

Preferably, the polyenylpyrrole derivative used in preparation of anti-oral cancer drugs inhibits tumor sphere formation ability of the OSCC cell.

Preferably, the polyenylpyrrole derivative used in preparation of anti-oral cancer drugs inhibits xenograft tumorigenicity of the OSCC cell.

Preferably, the polyenylpyrrole derivative enhances expression of prostate apoptosis response-4 (Par-4) in the OSCC cell.

Preferably, the polyenylpyrrole derivative inhibits the expression interleukin-17 receptor A (IL-17RA) in the OSCC cell.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In order to learn features and functions of the present invention, please refer to the following embodiments and related description.

There are still unmet medical needs that remain in prevention, diagnosis and treatment of oral cancer so that the present invention provides a polyenylpyrrole derivative used in preparation of anti-oral cancer drugs to solve the problems.

For further explanation, please refer to the following embodiments to learn features and chemical structure of the present polyenylpyrrole derivative used in preparation of anti-oral cancer drugs.

Figure 1A:
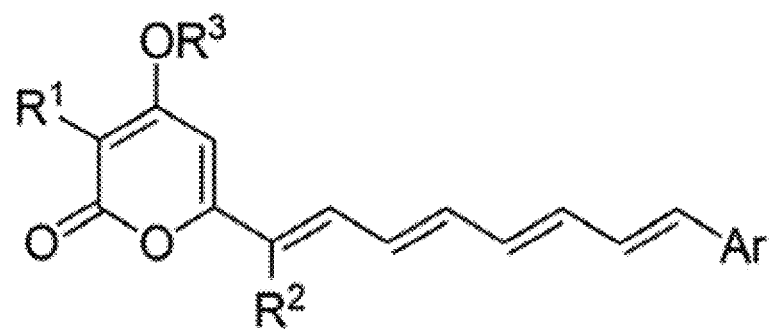
FIG. 1A is a chemical structure drawing of a basic skeleton of a polyenylpyrrole derivative according to the present invention.
Figure 1B:
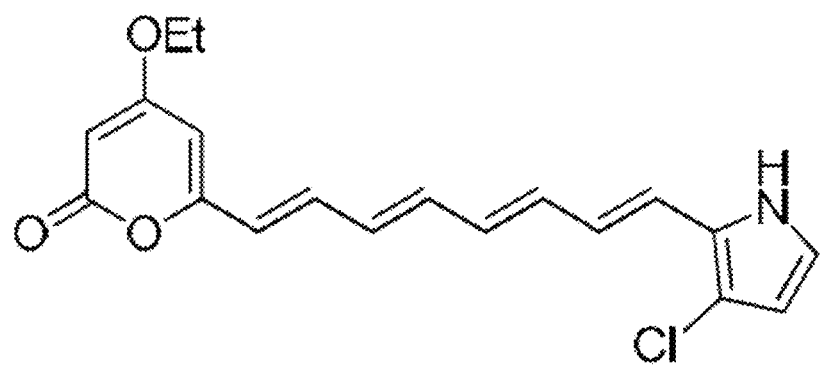
FIG. 1B is a chemical structure drawing of a polyenylpyrrole derivative according to the present invention.

Refer to FIG. 1A, a basic skeleton of a polyenylpyrrole derivative according to the present invention is revealed. A series of polyenylpyrrole derivatives is synthesized based on the basic skeleton of the polyenylpyrrole derivative shown in FIG. 1A by polyvinylpyrrole, auxarconjugatin A and 12E-isorumbrin. Also refer to FIG. 1B, a chemical structure of a polyenylpyrrole derivative according to the present invention is disclosed. The $R^1$ group, $R^2$ group and $R^3$ group of the basic skeleton of the polyenylpyrrole derivative are replaced by a hydrogen (H) atom, a H atom, and an ethyl (Et) group respectively to form the present polyenylpyrrole derivative. The Ar of the basic skeleton is replaced by 3-chloro-1H-pyrrol-2-group. The chemical structure of the polyenylpyrrole derivative obtained (alternative name: F236B) is shown in FIG. 1B.

The present polyenylpyrrole derivative is used to inhibit oral cancer cells. The oral cancer cell can be oral squamous cell carcinoma (OSCC) cell (SCC-15 cell line). The TW2.6 human oral squamous cell carcinoma (OSCC) cell line obtained from Asian people can also be used in cell proliferation assay.

Then a series of tests on proliferation, migration, movement, tumor spheroids formation abilities and xenograft tumorigenicity of the OSCC cells is done for confirming inhibition effect of the polyenylpyrrole derivative (F236B) on the OSCC cells.

Figure 2A:
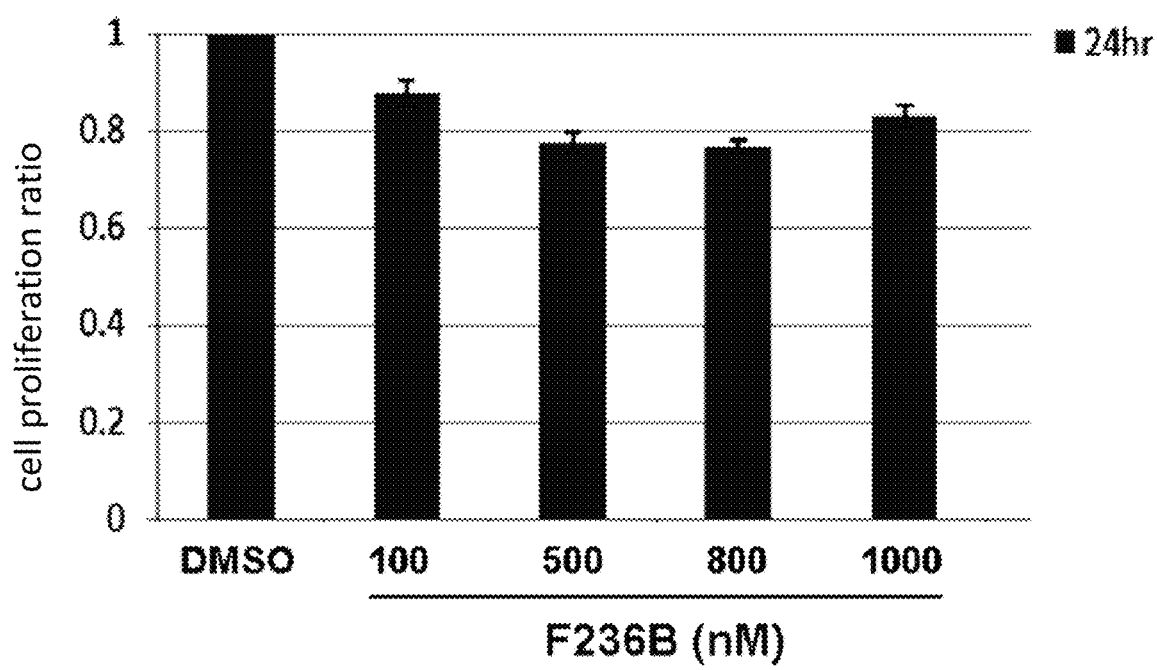
FIG. 2A-2F are bar graphs showing test results of the effect of a polyenylpyrrole derivative on proliferation ability and xenograft tumorigenicity of oral cancer cells according to the present invention.

Refer to FIG. 2A-2F, the test results of proliferation ability and xenograft tumorigenicity of oral cancer cells are revealed. MTT (3-(4,5-dimethylthiazol-2-yl)-2,5-diphenyltetrazolium bromide) assay is used for measuring cell proliferation. Add 3000 OSCC cells (SCC-15 and TW2.6) and 5000 immortalized cells (K2) into each well of a 96-well plate. Next day add the present polyenylpyrrole derivative (F236B) into the respective well and remove culture medium after 24 hours (hr) and 48 hr respectively. Then add MTT dissolved in culture medium (150 μL per well) except the background wells and react for 90 min. Lastly remove solution in the culture plate and add DMSO (150 μL per well) into the culture plate for dissolving the pigment. After being dissolved completely, use the ELISA machine to measure absorbance at 570 nm. The concentration of the polyenylpyrrole derivative (F236B) used is 10, 50, 80, 100, and 200 nM respectively, as results shown in FIG. 2A-2C. FIG. 2A shows the results of normal oral cells (K2) being treated with the polyenylpyrrole derivative (F236B) at higher concentration (100, 500, 800, and 1000 nM). Thus the test results indicated that polyenylpyrrole derivative (F236B) doesn't affect the proliferation of normal oral cells.

Figure 2B:
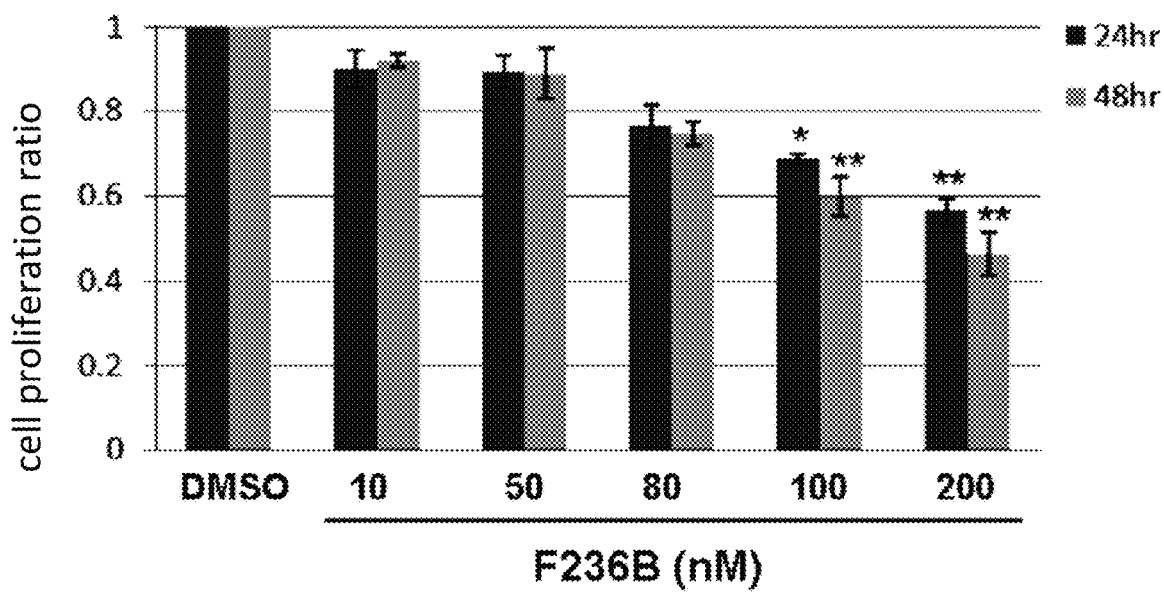
Figure 2C:
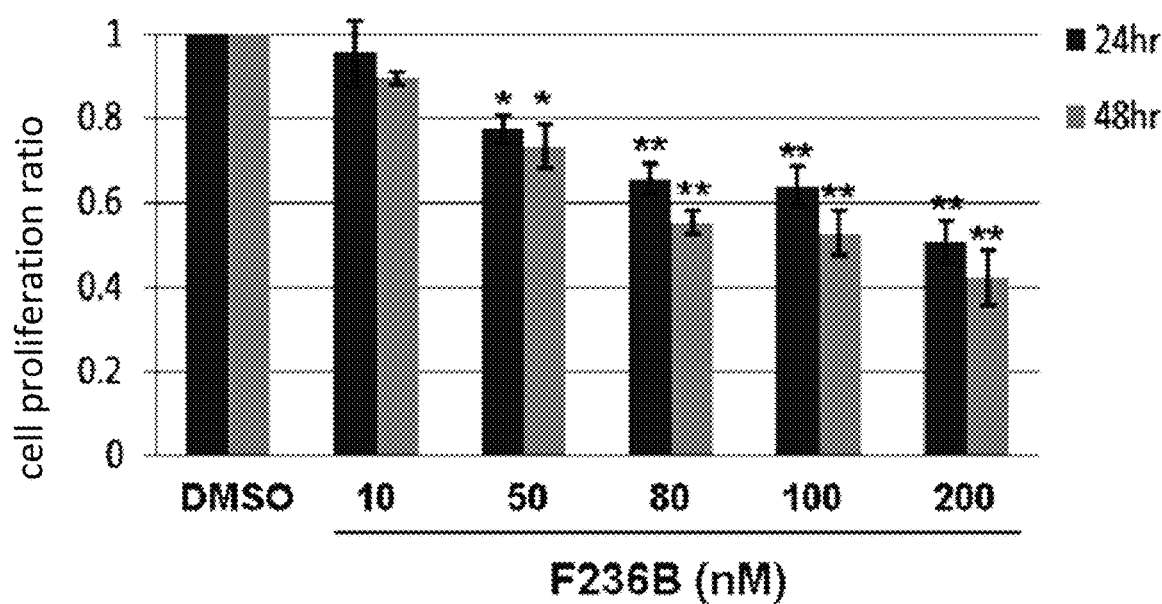

Refer to FIG. 2B, the test results of OSCC cells (SCC-15) treated with 10, 50, 80, 100, and 200 nM polyenylpyrrole derivative (F236B) respectively are revealed. The results show that the polyenylpyrrole derivative (F236B) inhibits proliferation of the OSCC cells (SCC-15). Also refer to FIG. 2C, test results of OSCC cells (TW2.6) treated with 10, 50, 80, 100, and 200 nM polyenylpyrrole derivative (F236B) respectively are disclosed. The results reveal that the polyenylpyrrole derivative (F236B) inhibits proliferation of the OSCC cells (TW2.6). Refer to FIG. 2A-2C, the results indicate that the polyenylpyrrole derivative (F236B) only inhibits proliferation of the OSCC cells (SCC-15 and TW2.6), while not affecting proliferation of the normal oral cells (K2). Moreover, the present polyenylpyrrole derivative (F236B) not only has effects on the OSCC cells of Western people (SCC-15) but also affects the OSCC cells of Asians (TW2.6). Thus the polyenylpyrrole derivative (F236B) can be widely used in the OSCC cells. In the previous tests for assessment of the effects of natural products on cancer cells, the unit of the concentration unit used is μM. Yet the concentration unit of the present polyenylpyrrole derivative (F236B) used is nM. By comparison, the present polyenylpyrrole derivative (F236B) inhibits proliferation of the OSCC cells without affecting normal oral cells (less negative effects on humans) at a lower concentration.

Figure 2D:
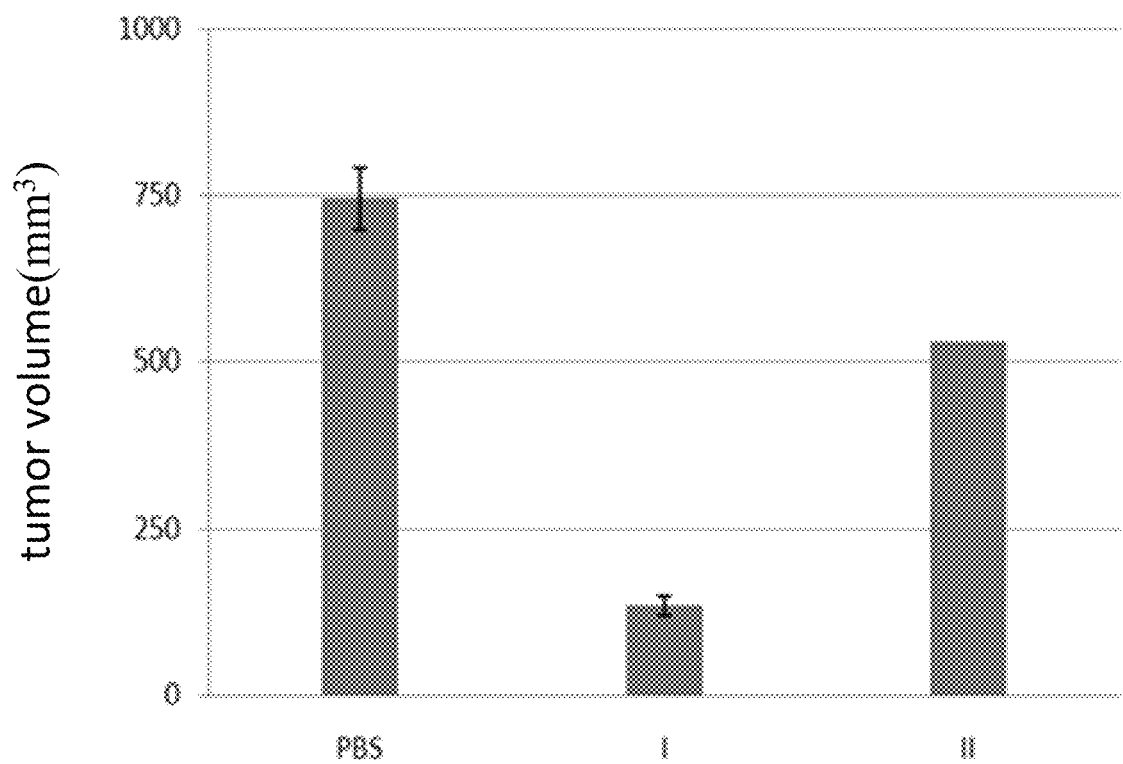
Figure 2E:
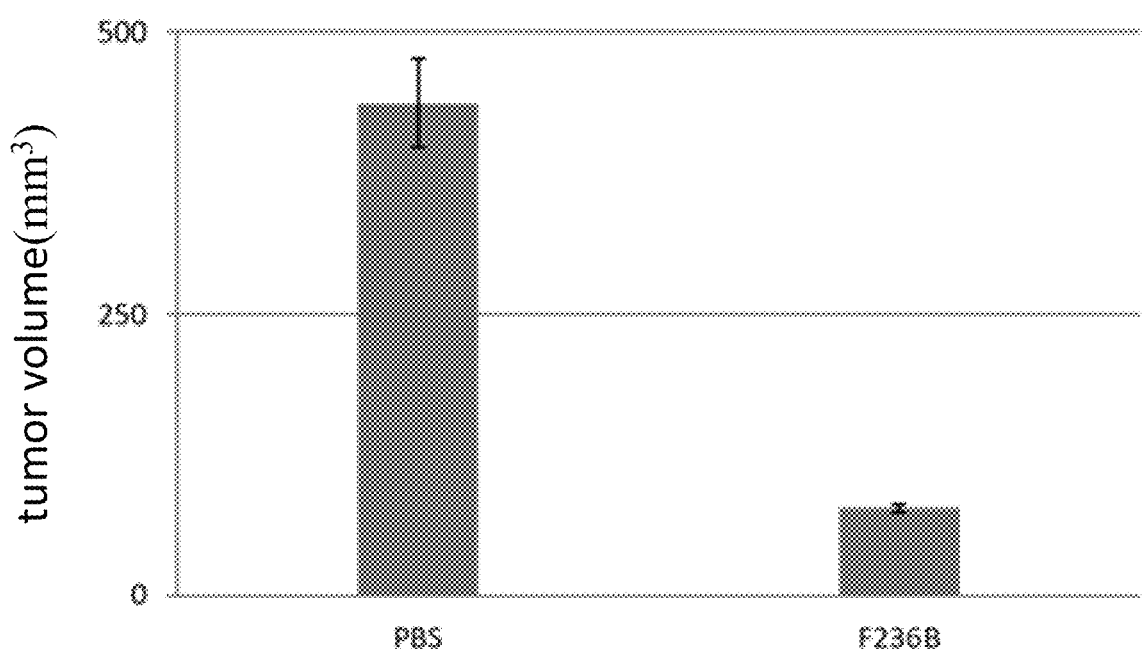
Figure 2F:
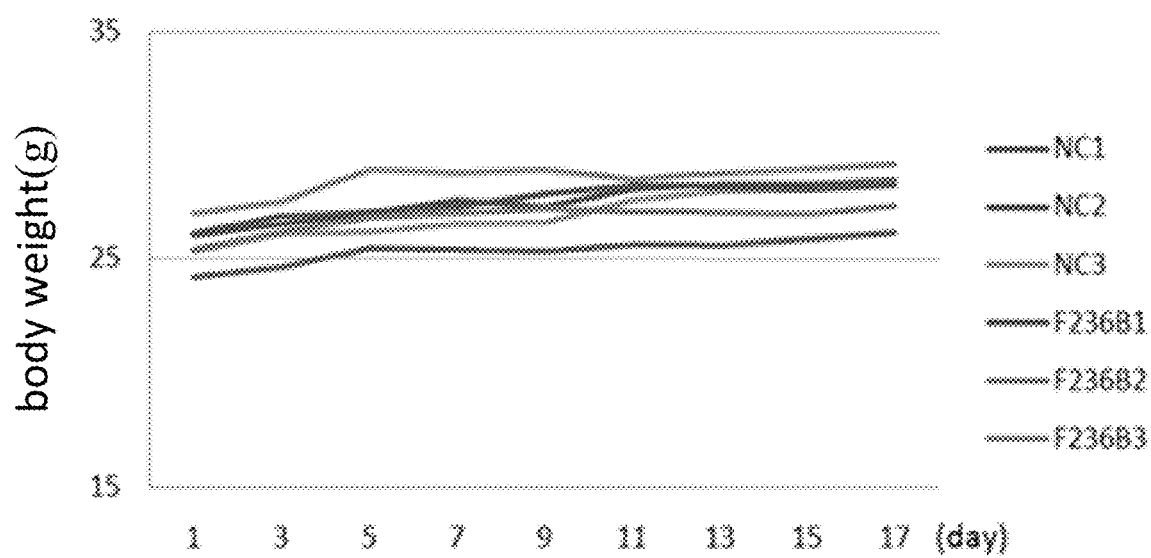

In order to learn whether in vivo test results of OSCC cells (SCC-15, TW2.6) are consistent with in vitro test results of the same, a cell-line-derived xenograft model (SCC-15 cell line) and a patient-derived xenograft (PDX) model of patients with oral cancers are used to test xenograft tumorigenicity of oral cancer cells and the results are shown in FIG. 2D-2F.

After approval of the institutional review board (IRB), oral cancer tissues of patients are collected at the Department of Otolaryngology, Hualien Tzu Chi Hospital during the period from Jul. 1, 2016 to Jun. 30, 2017. The PDX model has been established by immersing and washing the samples collected in Penicillin/Streptomycin diluted 2-fold with PBS, and using six-to-eight-week-old NOD-SCID male mice. After injection of a 0.01 mL/g body weight dose of ketamine/xylazine into a mouse, a 1.5×1.5 $cm^2$ skin surface at the right abdomen of the anesthetized mouse is treated with a depilatory agent to remove hair. Use tincture of iodine as a disinfectant and cut a wound of 30 mm-thickness on the mouse skin and suture the wound after tumor tissue being applied. During recovery period, the rearing cage is set on the heating pad and turned back to the rearing rack after recovery. After the surgery, observe the mouse day by day and then get the mouse out of the cage when the tumor reaches a diameter of about 1 cm. Next tumor is dissected and re-implanted into new recipient mice for 3-5 generation. Each generation thereafter is denoted P1, P2, P3, P4 and P5. Then the P3 mice are used to perform tests of the polyenylpyrrole derivative (F236B). The polyenylpyrrole derivative (F236B) at a dose of 1 mg/kg is subcutaneously injected into the neck of the mouse. Samples are taken when the tumor grows to a size with a diameter of about 1 cm.

As to the cell-line-derived xenograft model, six-to-eight-week-old NOD-SCID male mice are used. About $5 \times 10^6$ SCC-15 cells are subcutaneously injected into the right abdominal of the mouse. There are two experimental groups. The mouse in the first group (I) is injected with the polyenylpyrrole derivative (F236B) the day after being injected with the OSCC cells. In the second group (II), the mouse is injected with the polyenylpyrrole derivative (F236B) when the tumor grows to a size with a diameter of about 30 mm. The polyenylpyrrole derivative (F236B) at a dose of 1 mg/kg is subcutaneously injected into the neck of the mouse. Samples are taken when the cells grow to a size with a diameter of about 1 cm (21-day).

The results of the cell-line-derived xenograft model are shown in FIG. 2D. Compared with the control group that is injected with only PBS, the tumor volume of both the first group and the second group treated with F236B is significantly reduced. Refer to FIG. 2E, the results of PDX are disclosed and the tumor volume of the experimental group treated with F236B is dramatically decreased compared with the control group (injected with only PBS). Also refer to FIG. 2F, NC1, NC2, and NC3 are triplicated control groups (treated with PBS) while F236B1, F236B2, and F236B3 are triplicated experimental groups (treated with F236B). The weight of the mouse is not affected under the condition that the tumor growth is inhibited after being treated with F236B. The results in FIG. 2E and FIG. 2F demonstrate that the polyenylpyrrole derivative (F236B) inhibits xenograft tumorigenicity of the OSCC cells (SCC15 and TW2.6).

Furthermore, prostate apoptosis response-4 (Par-4) is a 38 kDa pro-apoptotic protein characterized by its ability to induce apoptosis in cancer cells. The protein is highly conserved in evolution of vertebrates. The previous studies have shown that Par-4 can directly induce apoptosis.

Figure 3A:
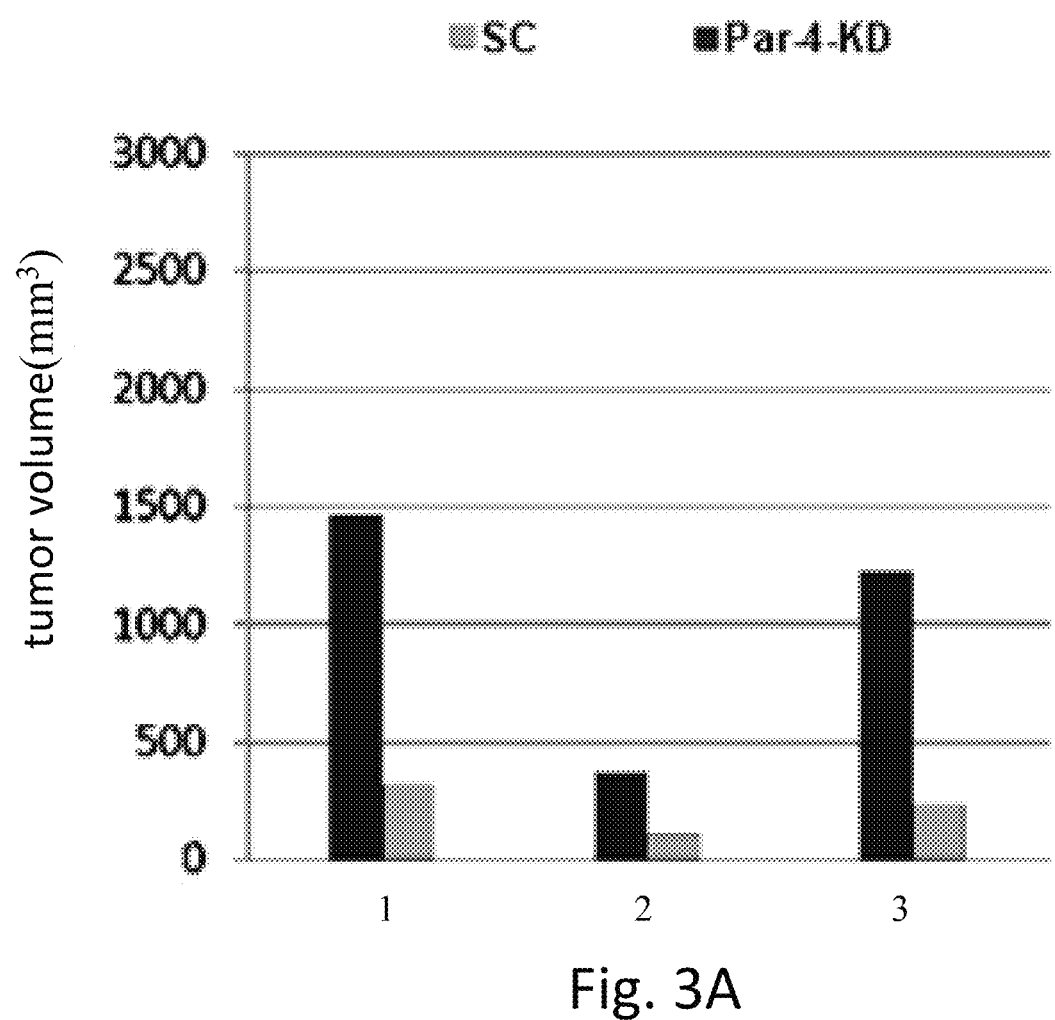
FIG. 3A-3E are bar graphs showing test results of the effect of a polyenylpyrrole derivative on expression of prostate apoptosis response-4 (Par-4) according to the present invention.
Figure 3B:
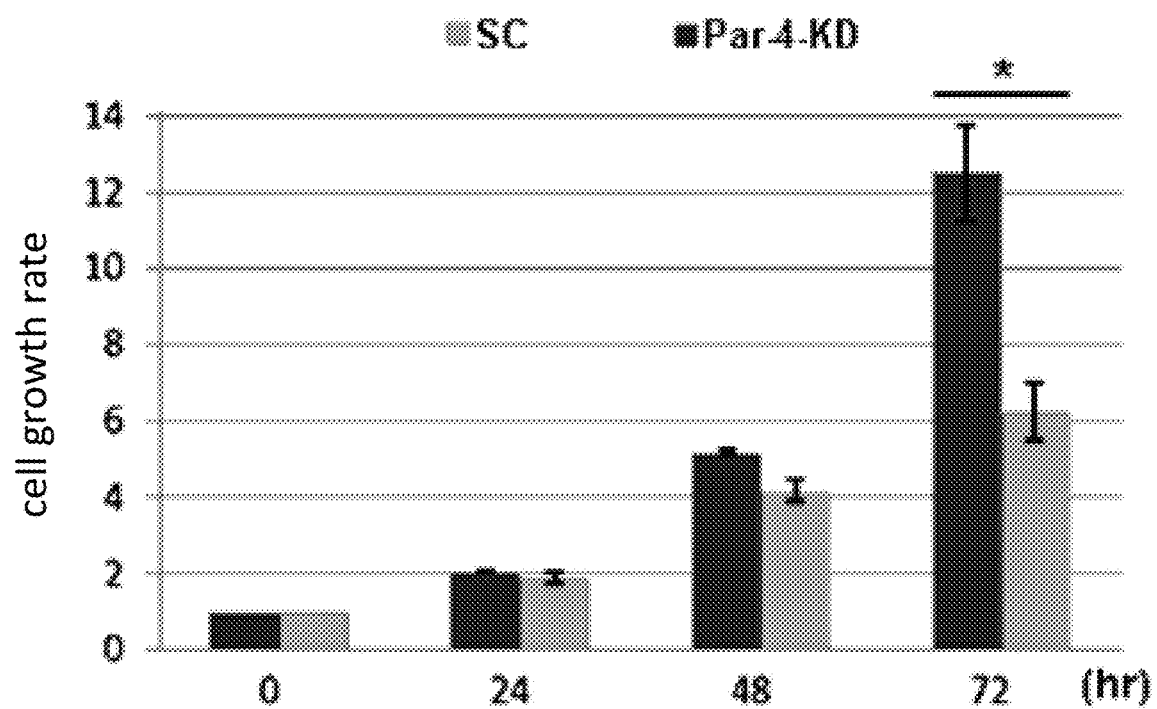

In order to learn whether Par-4 is involved in inhibition effect of F236B on the OSCC cells, the SCC-15 cell line with the knockdown Par-4 gene (called Par-4-KD) has been established in the present invention. The cells (Par-4-KD) are subcutaneously injected into the left and right abdomen of NOD-SCID male mice and tumors are removed after 3 weeks for comparing the size (3 sets of experiments). The results are shown in FIG. 3A and the tumor size of the Par-4-KD group is obviously larger than the SC group (SCC-15 cell line without the knockdown Par-4 gene). Refer to FIG. 3B, the growth rate of OSCC cells in the Par-4-KD group is apparently larger than that of OSCC cells in the SC group. The results in FIG. 3A and FIG. 3B indicate that Par-4 plays a role as a tumor suppressor in the OSCC cells.

Figure 3C:
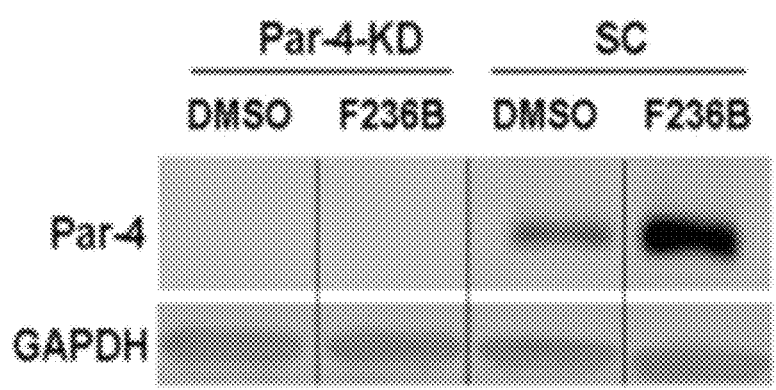
Figure 3D:
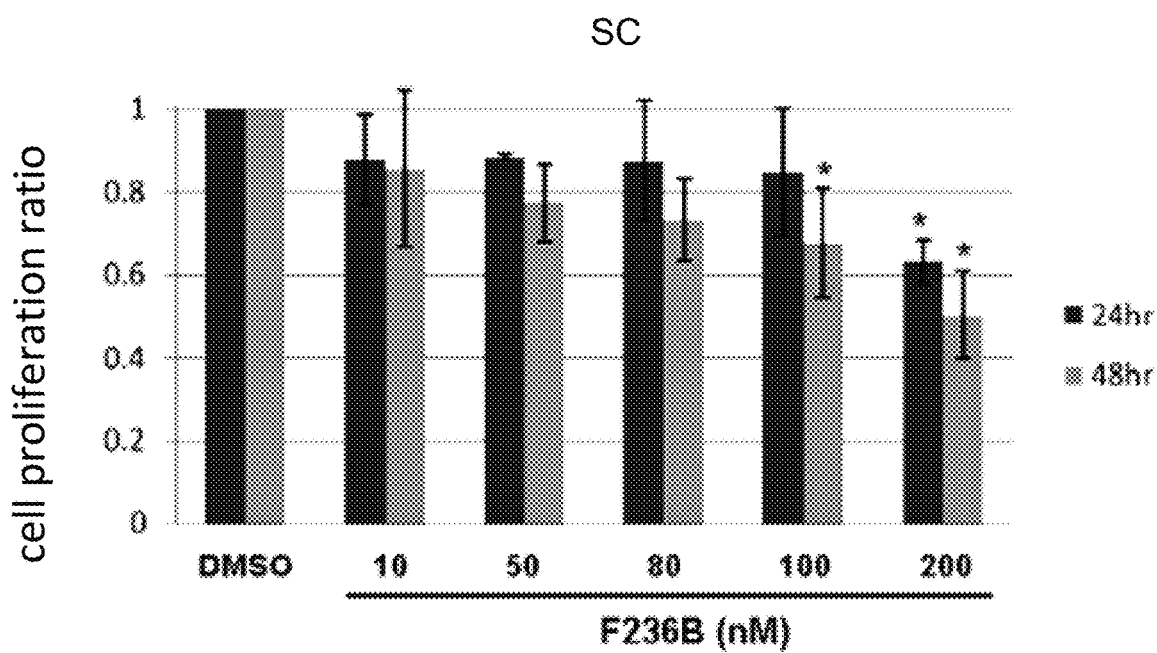
Figure 3E:
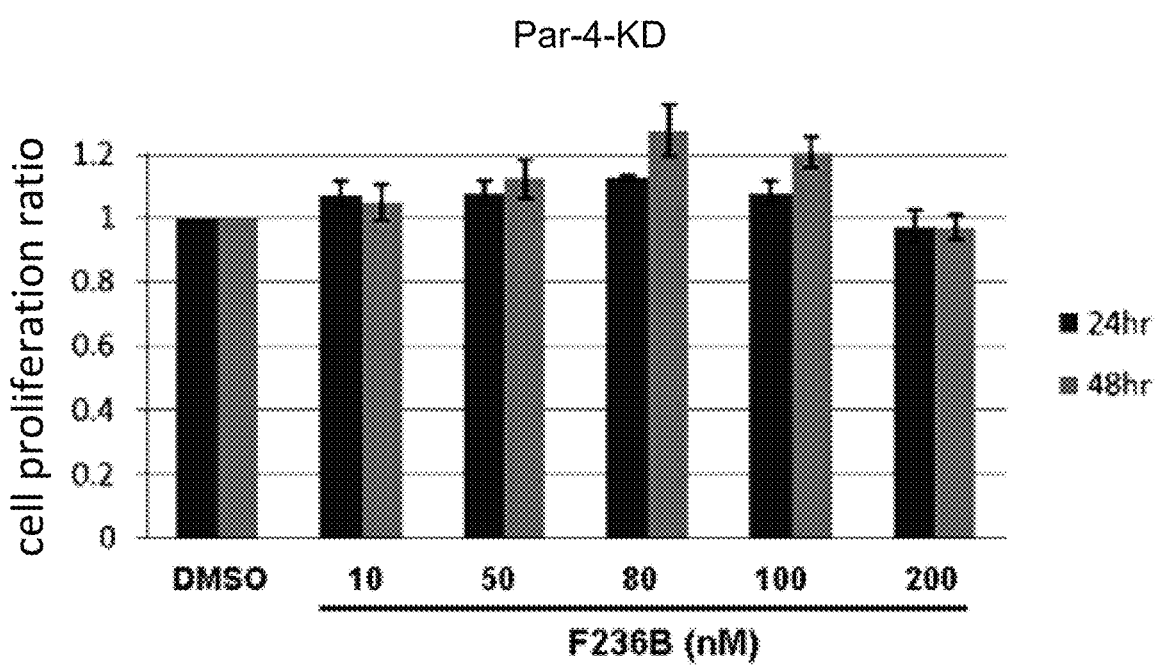

Refer to FIG. 3C, the polyenylpyrrole derivative (F236B) of the present invention enhances expression of Par-4 in the OSCC cells. Also refer to FIG. 3D and FIG. 3E. The results of the SC group (SCC-15 cell line without the knockdown Par-4 gene) treated with 10 nM, 50 nM, 80 nM, 100 nM, and 200 nM polyenylpyrrole derivative (F236B) for 24 hours and 48 hours respectively are shown in FIG. 3D. The results of the Par-4-KD group (SCC-15 cell line with the knockdown Par-4 gene) treated with 10 nM, 50 nM, 80 nM, 100 nM, and 200 nM polyenylpyrrole derivative (F236B) for 24 hours and 48 hours respectively are shown in FIG. 3E. After comparison of the results, the proliferation of OSCC cells in the SC group treated with F236B is apparently reduced owing to inhibition effect of the polyenylpyrrole derivative (F236B). Yet the Par-4-KD group is not.

Figure 4:
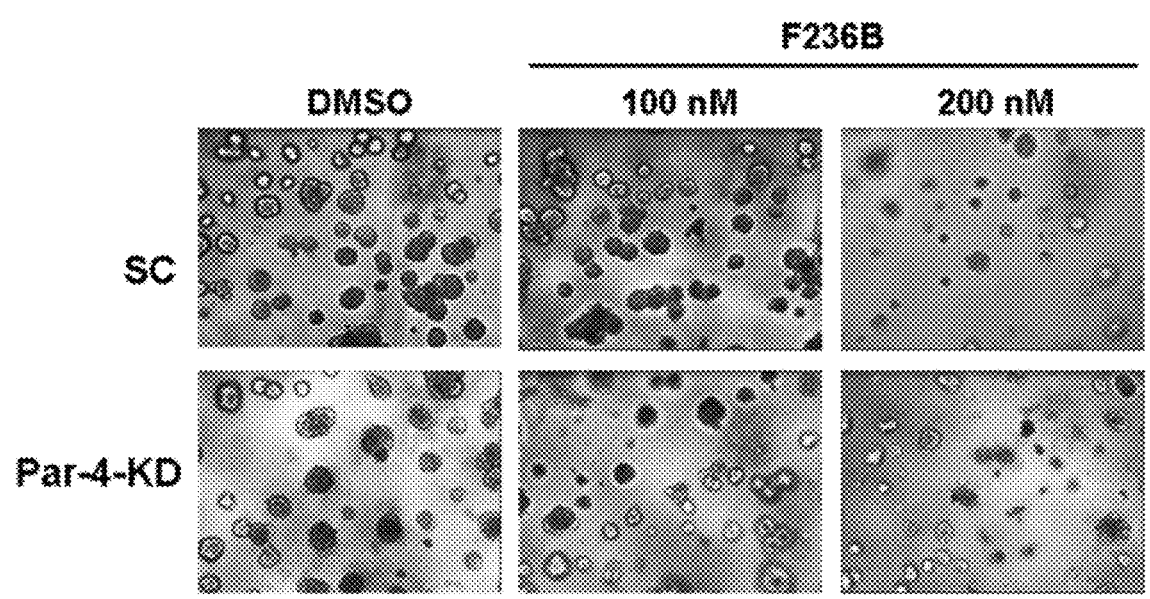
FIG. 4 shows test results of the effect of a polyenylpyrrole derivative on tumor sphere formation ability of oral cancer cells according to the present invention.

Refer to FIG. 4, the test results of the tumor sphere formation ability of the OSCC cells are shown. In order to culture cells (SCC-15) for tumor sphere formation, each well of a 24-well plate is coated with 150 µL growth factor reduced matrigel, then placed in 4° C. refrigerator and shaken for 15 minutes to make the growth factor reduced matrigel distribute evenly therein. Place in 37° C. incubator for 1 hour. After firm matrigel formation, each well is added with 5000 SCC-15 cells and change culture medium every day. The results are shown in FIG. 4. Compared with the Par-4-KD group, the SC group is inhibited by the polyenylpyrrole derivative (F236B) and its tumor sphere formation ability is obviously reduced.

Figure 5A:
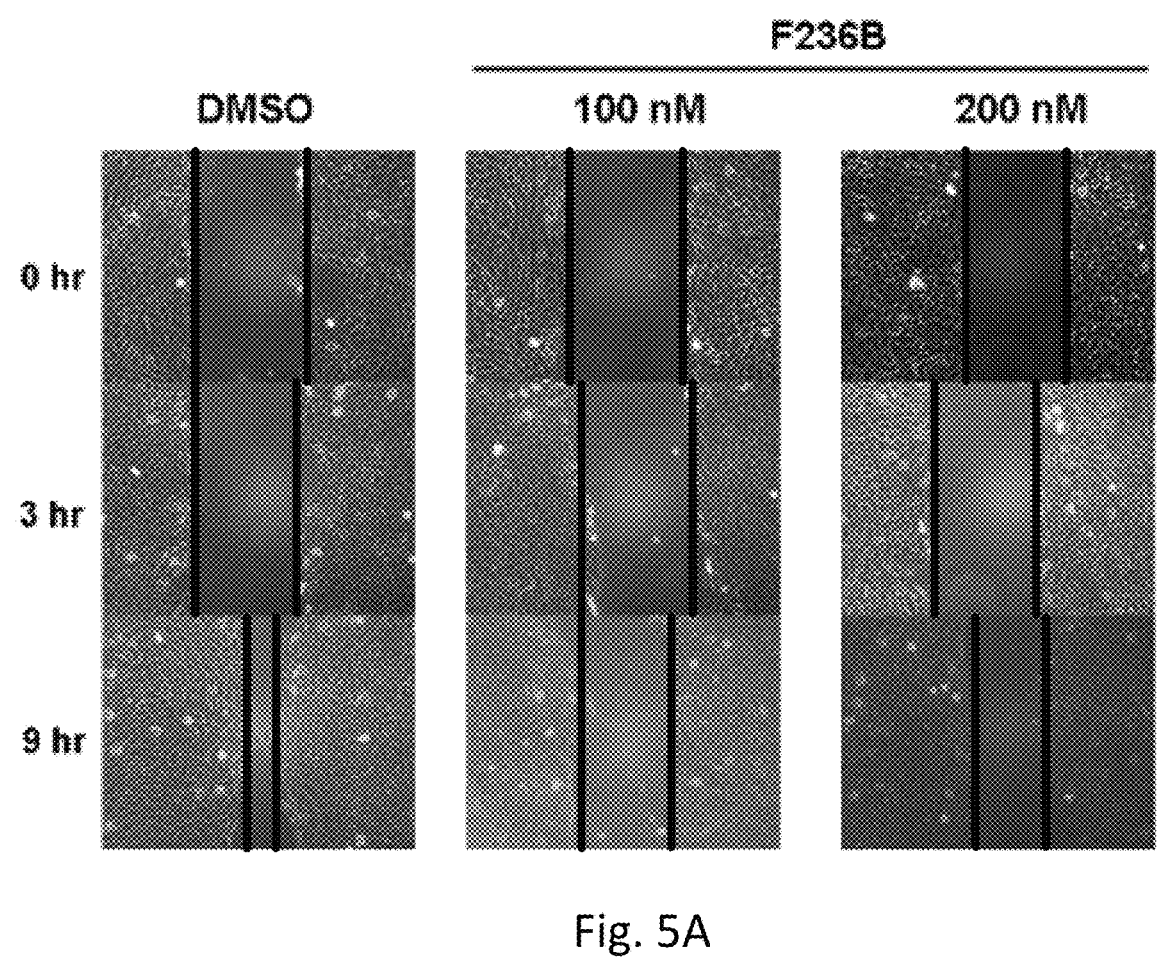
FIG. 5A-5B show test results of the effect of a polyenylpyrrole derivative on migration of oral cancer cells according to the present invention.
Figure 5B:
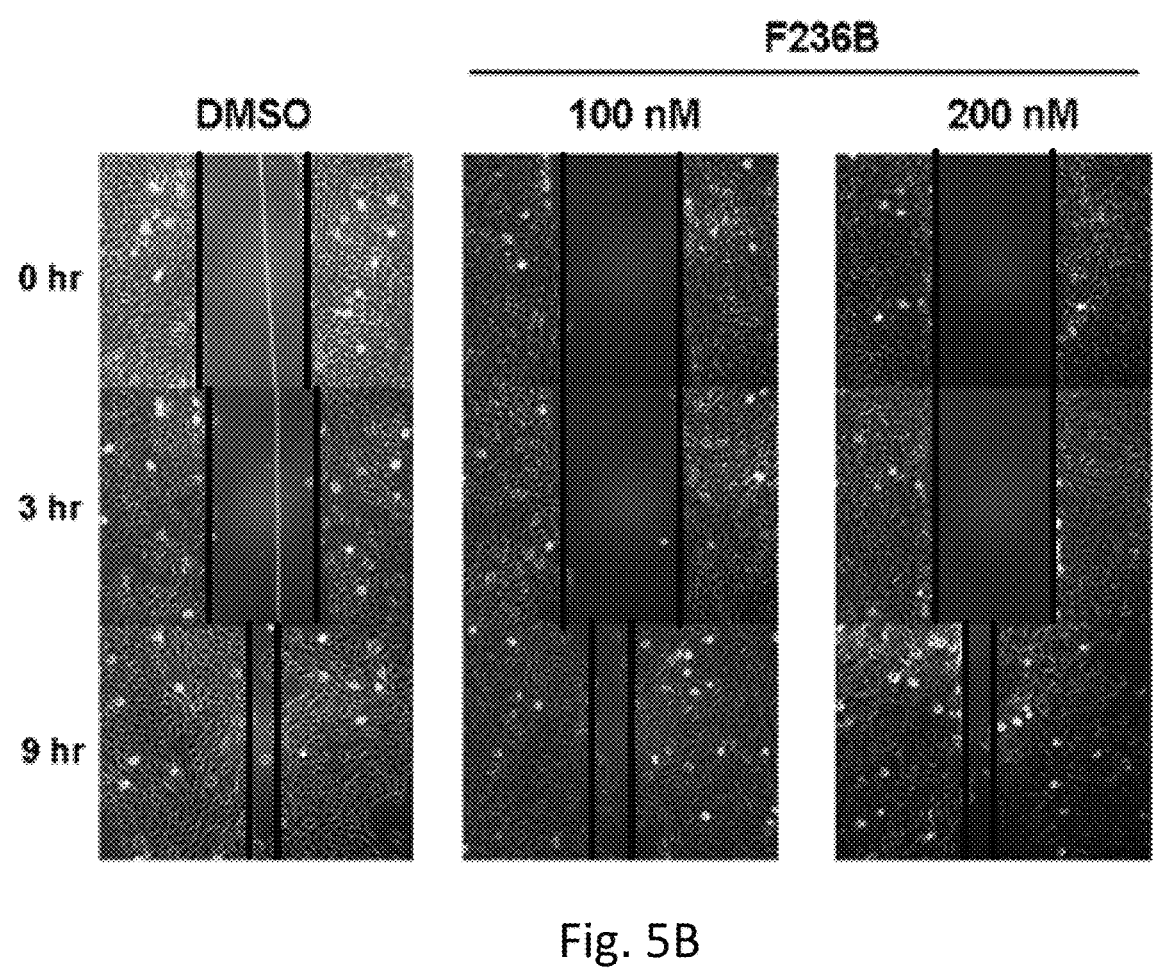
Figure 6:
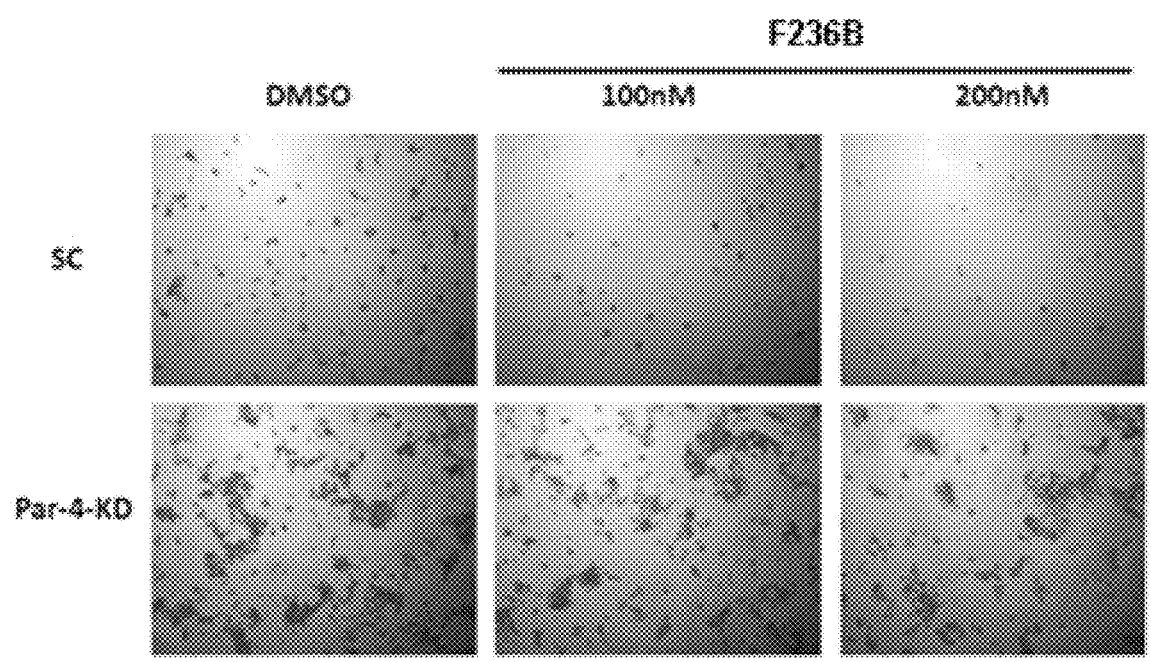
FIG. 6 shows test results of the effect of a polyenylpyrrole derivative on movement of oral cancer cells according to the present invention.

Then migration and movement of the Par-4-KD group and the SC group treated with polyenylpyrrole derivative (F236B) is tested and the results are shown in FIG. 5A-5B and FIG. 6.

Refer to FIG. 5A, the results of the SC group (SCC-15 cell line without the knockdown Par-4 gene) treated with 100 nM and 200 nM polyenylpyrrole derivative (F236B) for 0, 3 hr, and 9 hr respectively are displayed. The results of the Par-4-KD group (SCC-15 cell line with the knockdown Par-4 gene) treated with 100 nM and 200 nM polyenylpyrrole derivative (F236B) for 0, 3, and 9 hrs respectively are shown in FIG. 5B. The results are compared between two groups and it is found that migration ability of the SC group treated with polyenylpyrrole derivative (F236B) is clearly reduced owing to inhibition effect of polyenylpyrrole derivative (F236B) but the Par-4-KD group is not affected.

Refer to FIG. 6, a transwell assay is used for testing movement of tumor cells. A 24-well transwell chamber with 8.0 µm polycarbonate membrane (6.5 mm) therein is used. Add 100 µL serum free media into the upper layer and 500 µL media containing 10% serum into the lower layer. Then add 5000 cells (SCC-15) into the upper layer of each well, incubate overnight and add the polyenylpyrrole derivative (F236B). Remove the upper layer after 24 hrs and 48 hrs, respectively and wash 2 times with PBS. Add methanol (500 µL per well) at 4° C. for 1 hr for fixation and wash 2 times with PBS. Next, stain with crystal violet for 10 min and wash 2 times with PBS. Lastly observe and count the number of cells moved to the lower layer. As shown in FIG. 6, compared with the Par-4-KD group, the movement of the OSCC cells in the SC group is significantly reduced owing to suppression of the polyenylpyrrole derivative (F236B).

The results shown in FIG. 3A to FIG. 6 demonstrate the Par-4-KD group (SCC-15 cell line with the knockdown Par-4 gene) is not affected by the polyenylpyrrole derivative (F236B) compared with the SC group. And the inhibition effect of the polyenylpyrrole derivative (F236B) may be correlated with the Par-4.

Interleukin 17 is a pro-inflammatory cytokine. The previous research has found that IL-17 affects cellular development and exerts a synergistic effect with IL-1 and tumor necrosis factor (TNF). Interleukin-17 receptor (IL-17R) is a cytokine receptor which binds interleukin 17. In order to form this functional composite, IL-17RA and IL-17RC are required. The IL-17R receptor family further includes IL-17RB connected to IL-17B and IL-17E specifically, IL-17RD and IL-17RE. Moreover, IL-17RA is a receptor for IL-17. The clinical analysis has found that tumor tissues have higher IL-17RA expression than normal tissues in head and neck cancers while the expression of the rest receptors of the family is lower.

Figure 7:
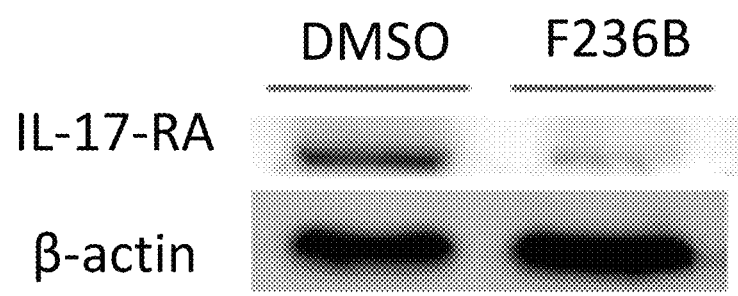
FIG. 7 shows test results of the effect of a polyenylpyrrole derivative on expression of interleukin-17 receptor A (IL-17 RA) according to the present invention.

Western blot is used to detect expression of IL-17RA in the OSCC cells (SCC-15) treated with the polyenylpyrrole derivative (F236B). The proteins are separated by SDS-PAGE gel and then transferred to a Polyvinylidene difluoride (PVDF) membrane. Then soak in 5% BSA (bovine serum albumin) for 1 hour for blocking. After removal of BSA and addition of primary antibodies, place the membrane in 4° C. refrigerator with constant shaking for 16 hr and wash 3 times with TBST-Tween20 (TBST) (each takes 15 min). Next add secondary antibodies and shake at room temperature for 1 hour. Then wash 3 times with TBST and each step takes 15 min. Lastly use enhanced chemiluminescent (ECL) reagent (RPN2106 ECL™ Western Blotting Reagent) for imaging and UVP BioSpectrum to detect images. The results shown in FIG. 7 indicate the expression of IL-17RA in the F236B group (treated with F236B) is obviously inhibited by the polyenylpyrrole derivative (F236B), much lower than the expression of IL-17RA in the control group (DMSO group, with no F236B). Therefore, the reduction effect of the polyenylpyrrole derivative (F236B) on the expression of IL-17RA is associated with the tumor-suppressor function of the polyenylpyrrole derivative (F236B).

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A polyenylpyrrole derivative used in preparation of anti-oral cancer drugs is used to inhibit oral cancer cells; wherein the polyenylpyrrole derivative has a structural formula shown in the diagram below, including a hydrogen (H) atom and an ethyl (Et) group:

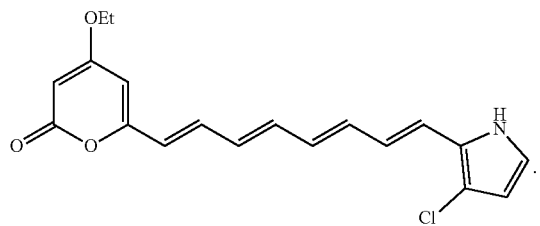 [SMILES: CCOc1cc(/C=C/C=C/C=C/C=C/c2[nH]ccc2Cl)oc(=O)c1]

2. The polyenylpyrrole derivative as claimed in claim 1, wherein the oral cancer cell is oral squamous cell carcinoma (OSCC) cell.

3. The polyenylpyrrole derivative as claimed in claim 2, wherein the polyenylpyrrole derivative inhibits proliferation ability of the OSCC cell.

4. The polyenylpyrrole derivative as claimed in claim 2, wherein the polyenylpyrrole derivative inhibits migration ability of the OSCC cell.

5. The polyenylpyrrole derivative as claimed in claim 2, wherein the polyenylpyrrole derivative inhibits movement ability of the OSCC cell.

6. The polyenylpyrrole derivative as claimed in claim 2, wherein the polyenylpyrrole derivative inhibits tumor sphere formation ability of the OSCC cell.

7. The polyenylpyrrole derivative as claimed in claim 2, wherein the polyenylpyrrole derivative inhibits xenograft tumorigenicity of the OSCC cell.

8. The polyenylpyrrole derivative as claimed in claim 2, wherein the polyenylpyrrole derivative enhances expression of prostate apoptosis response-4 (Par-4) in the OSCC cell.

9. The polyenylpyrrole derivative as claimed in claim 2, wherein the polyenylpyrrole derivative inhibits expression of interleukin-17 receptor A (IL-17RA) in the OSCC cell.

* * * * *